United States Patent
Smith, Sr.

(10) Patent No.: US 9,913,583 B2
(45) Date of Patent: Mar. 13, 2018

(54) HEALTH MONITORING SYSTEM USING OUTWARDLY MANIFESTED MICRO-PHYSIOLOGICAL MARKERS

(71) Applicant: Rememdia LC, Salt Lake City, UT (US)

(72) Inventor: Fraser Smith, Sr., Salt Lake City, UT (US)

(73) Assignee: Rememdia LC, Salt Lake City, UT (US)

( * ) Notice: Subject to any disclaimer, the term of this patent is extended or adjusted under 35 U.S.C. 154(b) by 174 days.

(21) Appl. No.: 14/789,750

(22) Filed: Jul. 1, 2015

(65) Prior Publication Data

US 2017/0000356 A1    Jan. 5, 2017

(51) Int. Cl.
| | |
|---|---|
| *A61B 5/00* | (2006.01) |
| *G06T 7/00* | (2017.01) |
| *G06F 19/00* | (2011.01) |
| *A61B 5/0205* | (2006.01) |
| *A61B 5/16* | (2006.01) |

(Continued)

(52) U.S. Cl.
CPC ........ *A61B 5/02055* (2013.01); *A61B 5/0022* (2013.01); *A61B 5/0077* (2013.01); *A61B 5/7275* (2013.01); *G06F 19/3431* (2013.01); *G06F 19/3443* (2013.01); *G06T 7/0016* (2013.01); *A61B 5/11* (2013.01); *A61B 5/1128* (2013.01); *A61B 5/14551* (2013.01); *A61B 5/165* (2013.01); *A61B 5/4803* (2013.01); *A61B 5/4806* (2013.01); *A61B 5/6898* (2013.01); *A61B 5/7257* (2013.01); *A61B 2576/00* (2013.01); *G06T 2207/10024* (2013.01); *G06T 2207/30076* (2013.01)

(58) Field of Classification Search
CPC . A61B 5/7275; A61B 5/0077; G06F 19/3431; G06T 7/0016

See application file for complete search history.

(56) References Cited

U.S. PATENT DOCUMENTS

| | | | |
|---|---|---|---|
| 4,653,498 A | | 3/1987 | New, Jr. et al. |
| 5,882,931 A | * | 3/1999 | Petersen ............ A61B 5/14507 422/108 |

(Continued)

OTHER PUBLICATIONS

Bigio et al., Ultraviolet and visible spectroscopies for tissue diagnostics: fluorescence spectroscopy and elastic-scattering spectroscopy, Phys. Med. Biol., 1997, pp. 803-814, IOP Publishing Ltd, United Kingdom.

(Continued)

*Primary Examiner* — William Levicky (57) ABSTRACT

A camera coupled to a processor is disclosed. The camera is configured to capture images of the subject. The processor is configured to amplify microscopic temporal variations between the images of the subject and generate a profile of at least one microscopic temporally detected physiological variation of the subject. The processor is further configured to compare the profile of the subject to a pre-existing first aggregate profile of a plurality of third-party subjects, said aggregate profile corresponding to the at least one microscopic temporally detected physiological variation of the third-party subjects, the aggregate third-party profile corresponding to a known state of the third-party subjects.

22 Claims, 2 Drawing Sheets

(51) Int. Cl.
*A61B 5/11* (2006.01)
*A61B 5/1455* (2006.01)

(56) References Cited

U.S. PATENT DOCUMENTS

| | | | |
|---|---|---|---|
| 7,365,839 B2 | 4/2008 | Ferguson et al. | |
| 8,179,418 B2 | 5/2012 | Wright et al. | |
| 2003/0112921 A1 | 6/2003 | Lang et al. | |
| 2004/0008219 A1* | 1/2004 | Sarel | G06F 19/3431 |
| | | | 715/700 |
| 2007/0249952 A1* | 10/2007 | Rubin | G04G 15/003 |
| | | | 600/544 |
| 2007/0293781 A1 | 12/2007 | Sims et al. | |
| 2009/0244485 A1 | 10/2009 | Walsh et al. | |
| 2010/0125175 A1 | 5/2010 | Vallone | |
| 2010/0166252 A1* | 7/2010 | Ahmed | A61B 5/14551 |
| | | | 382/100 |
| 2010/0305633 A1* | 12/2010 | Aziz | A61N 1/39 |
| | | | 607/3 |
| 2011/0117014 A1 | 5/2011 | Norenberg | |
| 2011/0142413 A1* | 6/2011 | Kang | A61B 5/165 |
| | | | 386/234 |
| 2012/0215075 A1 | 8/2012 | Surace et al. | |
| 2012/0221310 A1* | 8/2012 | Sarrafzadeh | A61B 5/0205 |
| | | | 703/11 |
| 2014/0039323 A1 | 2/2014 | Spector | |
| 2014/0072190 A1 | 3/2014 | Wu et al. | |
| 2014/0200419 A1 | 7/2014 | Ermakov et al. | |
| 2014/0200826 A1 | 7/2014 | Centola et al. | |
| 2014/0350961 A1 | 11/2014 | Csurka et al. | |
| 2017/0000392 A1 | 1/2017 | Smith | |
| 2017/0367580 A1 | 12/2017 | DiMaio et al. | |

OTHER PUBLICATIONS

Gandjbakhche et al., Quantitative Fluorescent Imaging of Specific Markers of Diseased Tissue, IEEE Journal of Selected Topics in Quantum Electronics, Dec. 1996, pp. 914-921, vol. 2 No. 4.

Wang et al., Tissue refractive index as marker of disease, Journal of Biomedical Optics, Nov. 2011, 8 pages, vol. 16(11).

* cited by examiner

HEALTH MONITORING SYSTEM USING OUTWARDLY MANIFESTED MICRO-PHYSIOLOGICAL MARKERS

FIELD OF THE TECHNOLOGY

The present technology relates to improved devices, methods, and systems for monitoring the health of a subject. More particularly, the present technology relates to devices, methods, and systems for assessing the condition or health state of a subject based primarily on outwardly manifested physiological markers.

BACKGROUND OF THE TECHNOLOGY

The increasing complexity of healthcare is causing fragmentation of care compromising patient safety and hospital efficiency. Increased costs of healthcare corresponding to the volumes of data and difficulty in assessing the state of the patient compound problems associated with patient safety and efficient treatment. Many treatment options and diagnoses, however, are made as the result of acute conditions or conditions that are readily observable to the medical practitioner during an office visit precipitated by an acute medical event. It is believed that many health conditions (mental, emotional, and/or physiological) can be detected before they warrant significant medical attention and/or before significant adverse affects or symptoms are felt by the subject.

SUMMARY OF THE INVENTION

In light of the problems and deficiencies inherent in the prior art, disclosed herein are methods, devices, and systems configured to monitor outward indicators of the health of a subject and correlate those indicators to states of a patient that correspond to pre-treatment of a condition and/or treatment of a condition without an acute medical event. In one example discussed herein, a device is configured to monitor visible physiological conditions of a subject comprising a camera in communication with a processor. The camera is configured to capture at least a first and second image of the subject. The processor comprises executable code configured to amplify microscopic temporal variations between the first and second image of the subject and generate a profile of at least one microscopic temporally detected physiological variation of the subject. The processor is further configured to compare the profile of the subject to a pre-existing first aggregate profile of a plurality of third-party subjects, said aggregate profile corresponding to the at least one microscopic temporally detected physiological variation of the third-party subjects, said aggregate third-party profile corresponding to a known state of the third-party subjects. The processor is further configured to detect differences between the profile of the subject and the aggregate profile of the plurality of third-party subjects and determine a probability that a state of the subject corresponds to the known state of the third-party subjects.

In one aspect of the technology, a device configured to monitor visible physiological conditions of a subject, comprising a camera coupled to a processor. The camera is configured to capture at least a first and second image of the subject. The processor comprises executable code configured to amplify microscopic temporal variations between the first and second image of the subject and generate a profile of at least one microscopic temporally detected physiological variation of a portion of the subject. The processor is further configured to compare the profile of the subject to a pre-existing baseline aggregate profile of the subject, said baseline aggregate profile corresponding to the at least one microscopic temporally detected physiological variation of the portion of the subject. The processor is further configured to detect differences between the profile of the subject and the pre-existing baseline aggregate profile of the subject.

In one aspect of the technology, a mobile robotic medical device assistant configured to monitor visible physiological conditions of a subject comprises a mobile assembly comprising a motor, a camera and a processor. The camera is configured to capture at least a first and second image of the subject, said processor configured to amplify microscopic temporal variations between the first and second image of the subject and generate a profile of at least one microscopic temporally detected physiological variation corresponding to the subject. The processor is further configured to compare the profile of the subject to a pre-existing aggregate profile of third-party subjects, said aggregate profile corresponding to the at least one microscopic temporally detected physiological variation of the plurality of third-party subjects. The processor is further configured to detect differences or similarities between the profile of the subject and the aggregate profile of the third-party subjects.

BRIEF DESCRIPTION OF THE DRAWINGS

The present technology will become more fully apparent from the following description and appended claims, taken in conjunction with the accompanying drawings. Understanding that these drawings merely depict exemplary aspects of the present technology they are, therefore, not to be considered limiting of its scope. It will be readily appreciated that the components of the present technology, as generally described and illustrated in the figures herein, could be arranged and designed in a wide variety of different configurations. Nonetheless, the technology will be described and explained with additional specificity and detail through the use of the accompanying drawings in which:

DETAILED DESCRIPTION OF EXEMPLARY ASPECTS OF THE TECHNOLOGY

The following detailed description of exemplary aspects of the technology makes reference to the accompanying drawings, which form a part hereof and in which are shown, by way of illustration, exemplary aspects in which the technology can be practiced. While these exemplary aspects are described in sufficient detail to enable those skilled in the art to practice the technology, it should be understood that other aspects can be realized and that various changes to the technology can be made without departing from the spirit and scope of the present technology. Thus, the following more detailed description of the aspects of the present technology is not intended to limit the scope of the technology, as claimed, but is presented for purposes of illustration only and not limitation to describe the features and characteristics of the present technology, to set forth the best mode of operation of the technology, and to sufficiently enable one skilled in the art to practice the technology. Accordingly, the scope of the present technology is to be defined solely by the appended claims. The following detailed description and exemplary aspects of the technology will be best understood by reference to the accompanying drawings and description, wherein the elements and features of the technology are designated by numerals throughout the drawings and described herein.

As used in this specification and the appended claims, the singular forms "a," "an" and "the" include plural referents unless the context clearly dictates otherwise. Thus, for example, reference to "a layer" includes a plurality of such layers.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps can be performed, and certain of the stated steps can possibly be omitted and/or certain other steps not described herein can possibly be added to the method.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments described herein are, for example, capable of operation in other orientations than those illustrated or otherwise described herein. Objects described herein as being "adjacent to" each other can be in physical contact with each other, in close proximity to each other, or in the same general region or area as each other, as appropriate for the context in which the phrase is used.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness can in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element can still actually contain such item as long as there is no measurable effect thereof.

As used herein, the term "about" is used to provide flexibility to a range endpoint by providing that a given value can be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms."

An initial overview of technology is provided below and specific technology is then described in further detail. This initial summary is intended to aid readers in understanding the technology more quickly, but is not intended to identify key or essential features of the technology, nor is it intended to limit the scope of the claimed subject matter.

Broadly speaking, the technology described herein resides in a device configured to monitor micro-visible physiological conditions of a subject. A camera is coupled to or otherwise in communication with a processor and configured to capture at least a first and second image of the subject. The processor comprises executable code configured to amplify temporal variations between the first and second image of the subject and generate a profile of at least one microscopic temporally detected physiological variation of the subject. The variations are intended to be correlated with known states of third-party data. A state of the subject can include a physical condition (e.g., heart attack), a mental condition (e.g., aggravated psychosis), or an emotional condition (e.g., severe depression). The physiological variation can include changes in pulse, skin coloration, volume of sweat, etc. The processor is further configured to compare the profile of the subject to a pre-existing aggregate profile of a plurality of third-party subjects. The aggregate profile of the third-party subjects corresponds to the at least one microscopic temporally detected physiological variation of the principal subject. The physiological variation corresponds to a known state of the third-parties. A process is employed to determine the probability that the state of the principal subject is similar to (or dissimilar to) the known state of the third-parties. For example, if the variations of the subject being examined relates to the correlation between skin coloration and the subject's emotional state, the aggregate profile compared to the subject's profile is an aggregate profile of third-parties having a known emotional state and exhibiting a micro-observed skin coloration pattern. The processor is configured to detect differences and/or similarities between the profile of the subject and the aggregate profile of the plurality of third-party subjects and correlate the similarities and/or differences between the two.

In one aspect, a baseline state of the subject can be determined based on a plurality of measurements taken of the subject. The processor can be configured to compare a current profile of the subject to the baseline profile. It can also be configured to compare the current profile to a pre-existing second aggregate profile of a plurality of third-party subjects, wherein said second aggregate profile of the plurality of third-party subjects corresponds to a modified (or a diseased, agitated, abnormal, etc.) state of the plurality of third-party subjects. The profiles (of the subject and/or third parties) can be stored in a database that is modifiable with new data. That is, the aggregate profile can be modified by each individual measurement of a subject. In one aspect, however, the aggregate profile used in a comparison between a current subject can be time delimited and/or exclude historical data from the same subject. For example, the aggregate profile used in a comparison between third-parties and a subject is not modified by current subject measurements or, alternatively, any measurements taken of the subject within a predetermined previous time period (e.g., 1 day, 1 week, or 1 month, etc.).

In accordance with one aspect of the technology, a time series of color values at any spatial location (e.g., a pixel) of images of a subject can be taken and microscopic variations amplified in a given temporal frequency band of interest. The processor (or user) can select and then amplify a band of temporal frequencies including, as one non-limiting example, plausible human heart rates. The amplification reveals the variation of redness as blood flows through the face, neck, and/or ears. For this application, lower spatial frequencies can be temporally filtered to allow a subtle input signal to rise above the camera sensor and quantization noise. The temporal filtering approach not only amplifies color variation, but can also reveal low-amplitude motion. For example, the method can enhance the subtle motions of the eyes of a subject. It can also reveal other subtle facial movements and/or movements of the body that are indicative (i.e., provide specific non-verbal cues) of different states of the subject.

The method's mathematical analysis can employ a linear approximation related to the brightness constancy assumption used in optical flow formulations. The method also can derive the conditions under which this approximation holds. This can lead to a multi-scale approach to magnify motion without feature tracking or motion estimation. The method studies and amplifies the variation of pixel values over time, in a spatially-multi-scale manner. The Eulerian approach (i.e., the approach described herein) to motion magnification does not explicitly estimate motion, but rather exaggerates motion by amplifying temporal color changes at fixed positions. The method can employ differential approximations that form the basis of optical flow algorithms.

In one aspect, the method can employ localized spatial pooling and bandpass filtering to extract and reveal visually the signal corresponding to motion. This primal domain analysis allows amplification and visualization of the pulse signal at each location on the face (or area observed) of a subject, for example. Nearly invisible changes in a dynamic environment can be revealed through Eulerian spatio-temporal processing of standard monocular video sequences. The method can be run in real time. An analysis of the link between temporal filtering and spatial motion shows that the method is suited to small displacements and lower spatial frequencies. A single framework can amplify both spatial motion and purely temporal changes (e.g., a heart pulse) and can be adjusted to amplify particular temporal frequencies.

In one aspect of the technology, a spatial decomposition module of a system first decomposes input images into different spatial frequency bands, then applies the same temporal filter to the spatial frequency bands. The outputted filtered spatial bands are then amplified by an amplification factor, added back to the original signal by adders, and collapsed by a reconstruction module to generate the output images. The temporal filter and amplification factors can be tuned to support different applications. The output images correlate to specific numerical values related to a base or "normal" state as well as a modified or "abnormal" state. For example, a baseline determination of the pulse of a subject under a "normal" set of circumstances can be measured and later compared with the pulse of the subject under a varied set of circumstances. The subject, for example, can be asked a series of questions to which the answer is known and the subject answers honestly (i.e., what is your name, how old are you). A series of other unknown questions can then be asked to determine if the subject's pulse changes. As noted herein, the blood flow through the patients, face, neck, and/or ears, the appearance of microscopic sweat, and other micro-movements of the subject can be detected and observed. The comparison of changes between the subject's outward appearance provides a method by which a health state of the subject can be predicted.

In one aspect, the method combines spatial and temporal processing to emphasize subtle temporal changes in video images of the subject. The method decomposes the video sequence into different spatial frequency bands. These bands might be magnified differently because (a) they might exhibit different signal-to-noise ratios or (b) they might contain spatial frequencies for which the linear approximation used in motion magnification does not hold. In the latter case, the method reduces the amplification for these bands to suppress artifacts. When the goal of spatial processing is to increase temporal signal-to-noise ratio by pooling multiple pixels, the method spatially low-pass filters the frames of the video and downsamples them for computational efficiency. In the general case, however, the method computes a full Laplacian pyramid.

The method then performs temporal processing on each spatial band. The method considers the time series corresponding to the value of a pixel in a frequency band and applies a bandpass filter to extract the frequency bands of interest. As one example, the method can select frequencies within the range of 0.4-4 Hz, corresponding to 24-240 beats per minute, if the user wants to magnify a pulse, for example. If the method extracts the pulse rate, it can employ a narrow frequency band around that value. The temporal processing is uniform for all spatial levels and for all pixels within each level. The method then multiplies the extracted bandpassed signal by a magnification factor $\alpha$. This factor can be specified by the user, and can be attenuated automatically. Next, the method adds the magnified signal to the original signal and collapses the spatial pyramid to obtain the final output. Since natural videos are spatially and temporally smooth, and since the filtering is performed uniformly over the pixels, the method implicitly maintains spatio-temporal coherency of the results. The present method can amplify small motion without tracking motion as in Lagrangian methods. Temporal processing produces motion magnification using an analysis that relies on the first-order Taylor series expansions common in optical flow analyses as explained in U.S. Pub. 2014/0072190 to Wu et al. which is incorporated herein by reference in its entirety.

To process an input image by Eulerian video magnification, a user (or pre-programmed processor) can (1) select a temporal bandpass filter; (2) select an amplification factor, $\alpha$; (3) select a spatial frequency cutoff (specified by spatial wavelength, $\lambda_c$) beyond which an attenuated version of $\alpha$ is used; and (4) select the form of the attenuation for $\alpha$—either force $\alpha$ to zero for all $\lambda < \lambda_c$, or linearly scale $\alpha$ down to zero. The frequency band of interest can be chosen automatically in some cases, but it is often important for users to be able to control the frequency band corresponding to their application. In our real-time application, the amplification factor and cutoff frequencies are all customizable by the user. In one aspect of the technology, the camera assets described herein can be configured to detect wavelengths of light in a variety of wavelengths of light. For example, in one aspect, the camera can be configured to detect a first band of wavelengths of light ranging from approximately 150 to 400 nm, a second band of wavelengths of light ranging from approximately 400 to 700 nm, and a third band of wavelengths of light ranging from approximately 700 to 1100 nm. Advantageously, data regarding the subject's state which may not be observable in the conventional visible spectrum of light (i.e., 400 to 700 nm) can be observed and used in connection with predicting the state of the subject.

In one aspect, Eulerian video magnification can be used to amplify subtle motions of blood vessels (e.g., a radial artery and an ulnar artery) arising from blood flow. In this aspect, the temporal filter is tuned to a frequency band that includes the heart rate (e.g., 0.88 Hz (53 bpm) and the amplification factor can be set to $\alpha=10$. To reduce motion magnification of irrelevant objects, a user-given mask amplifies the area near the wrist only. Movement of the radial artery and the ulnar artery can barely be seen in an unprocessed input video, but is significantly more noticeable in the motion-magnified output. While more noticeable to the naked eye, the motion is more pronounced and hence more useable in detecting and diagnosing changes in the emotional, mental, or physiological state of a patient. Similar approaches can be employed in observing discrete areas of the body (e.g., the eye(s) or face).

In one aspect of the technology, the process selects the temporal bandpass filter to pull out the motions or signals to be amplified. The choice of filter is generally application dependent. For motion magnification, a filter with a broad passband can be used; for color amplification of blood flow, a narrow passband produces a more noise-free result. Ideal bandpass filters can be used for color amplification, since they have passbands with sharp cutoff frequencies. Low-order IIR filters can be useful for both color amplification and motion magnification and are convenient for a real-time implementation. In general, two first-order lowpass IIR filters with cutoff frequencies $\omega_1$ and $\omega_h$ can be used to construct an IIR bandpass filter. The process selects the desired magnification value, $\alpha$, and spatial frequency cutoff, $\lambda_c$. Various $\alpha$ and $\lambda_c$ values can be used to achieve a desired result. The user can select a higher $\alpha$ that violates the band to exaggerate specific motions or color changes at the cost of increasing noise or introducing more artifacts. In one aspect of the technology, the Eularian motion magnification confirms the accuracy of a heart rate estimate and verifies that the color amplification signal extracted from the method matches the photoplethysmogram, an optically obtained measurement of the perfusion of blood to the skin, as measured by the monitor.

The method takes a video as input and exaggerates subtle color changes and micro-motions. To amplify motion, the method does not perform feature tracking or optical flow computation, but merely magnifies temporal color changes using spatio-temporal processing. This Eulerian based method, which temporally processes pixels in a fixed spatial region, reveals informative signals and amplifies small motions in real-world videos. The Eulerian-based method begins by examining pixel values of two or more images. The method then determines the temporal variations of the examined pixel values. The method is designed to amplify only small temporal variations. While the method can be applied to large temporal variations, the advantage in the method is provided for small temporal variations. Therefore, the method can be optimized when the input video has small temporal variations between the images. The method can then apply signal processing to the pixel values. For example, signal processing can amplify the determined temporal variations, even when the temporal variations are small.

In one aspect of the technology, client computer(s)/devices and server computer(s) provide processing, storage, and input/output devices executing application programs and the like for use of the methods and processes described herein. Client computer(s)/devices can also be linked through communications network to other computing devices, including other client devices/processes and server computer(s). Communications network can be part of a remote access network, a global network (e.g., the Internet), a worldwide collection of computers, local area or wide area networks, and gateways that currently use respective protocols (TCP/IP, Bluetooth, etc.) to communicate with one another. Other electronic device/computer network architectures are suitable.

In accordance with one aspect, a computer can contain a system bus, where a bus is a set of hardware lines used for data transfer among the components of a computer or processing system. The bus is essentially a shared conduit that connects different elements of a computer system (e.g., processor, disk storage, memory, input/output ports, network ports, etc.) that enables the transfer of information between the elements. Attached to the system bus is an I/O device interface for connecting various input and output devices (e.g., keyboard, mouse, displays, printers, speakers, etc.) to the computer. A network interface allows the computer to connect to various other devices attached to a network. A memory provides volatile storage for computer software instructions and data used to implement an embodiment of the present invention (e.g., code detailed above). A disk storage provides non-volatile storage for computer software instructions and data used to implement an embodiment of the present invention. A central processor unit is also attached to the system bus and provides for the execution of computer instructions.

In one embodiment, the processor routines and data are a computer program product, including a computer readable medium (e.g., a removable storage medium such as one or more DVD-ROM's, CD-ROM's, diskettes, tapes, etc.) that provides at least a portion of the software instructions for the invention system. A computer program product can be installed by any suitable software installation procedure, as is well known in the art. In another aspect, at least a portion of the software instructions can also be downloaded over a cable, communication and/or wireless connection. In other aspects, the programs comprise a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present technology. In alternate aspects, the propagated signal can comprise an analog carrier wave or digital signal carried on the propagated medium. For example, the propagated signal can be a digitized signal propagated over a global network (e.g., the Internet), a telecommunications network, or other network. In one embodiment, the propagated signal can comprise a signal that is transmitted over the propagation medium over a period of time, such as the instructions for a software application sent in packets over a network over a period of milliseconds, seconds, minutes, or longer. In another embodiment, the computer readable medium of computer program product can be a propagation medium that the computer system can receive and read, such as by receiving the propagation medium and identifying a propagated signal embodied in the propagation medium, as described above for computer program propagated signal product. Generally speaking, the term "carrier medium" or transient carrier encompasses the foregoing transient signals, propagated signals, propagated medium, storage medium and the like.

Figure 2:
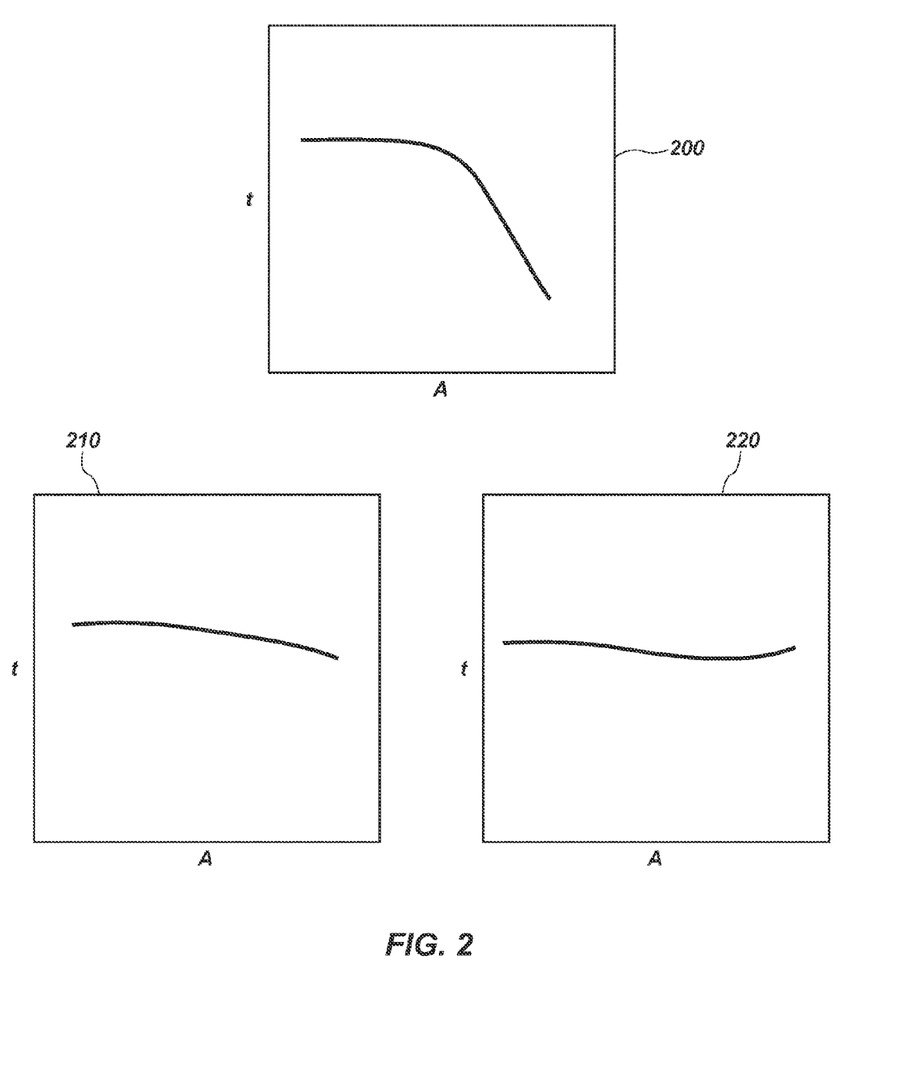
FIG. 2 is a plurality of diagrams illustrating aspects of the current technology.

In one aspect of the technology, datasets of baseline data related to subject observations are collected and a profile of subject characteristics is generated. For example, a profile of a subject in day-to-day conditions might include the subject's heartrate throughout the day during the subject's normal activities. The subject's temperature, facial expressions, etc. can also be included in the profile. FIG. 2 illustrates a graphical representation of a generic profile 200 generated for a microscopically detected change (delta) over time (t) of a subject. A graphical representation of a baseline profile (i.e., an aggregation of historical data) for the same subject is shown on 210. A graphical representation of an aggregate third-party profile is presented at 220. In each representation, the change (delta) of the same microscopically detected change (e.g., eye movement) over the same time period is presented.

Metadata associated with the subject's diet, sleeping patterns, and other activities can also be included in the profile. The subject's profile can be compared with his or her own profile in the past and used as a basis for determining the subject's mental, emotional, and/or physiological state. In another aspect of the technology, the subject's profile can be compared with an aggregate profile of third-parties to discern the subject's mental, emotional, and/or physiological state. In this manner, outwardly observable micro-indicators can be correlated with third-party mental, emotional, and physiological states to predict the subject's own mental, emotion, and/or physiological state. In one aspect, the subject's own profile can be that of a previous "normal" state (i.e., healthy) and/or a previous modified (i.e., not healthy) state.

In one aspect, aggregation includes normalization of a dataset limited by user-selected categories. Given a finite set of health-related categories, datasets can be grouped in categories. Non-limiting example categories include blood analyses, MRI images, medical history, medical prescriptions, family history, health habits, age, gender, weight, and/or race. Aggregated groups can further be grouped into subclasses as suits a particular analysis. In one non-limiting example, an aggregate profile is generated for outward micro-indicators of female subjects suffering from cancer and receiving chemotherapy. The aggregate profile can be used as a baseline comparison for a specific subject falling into the same category to determine the subject's deviation from or similarity to the aggregate profile. In each category, and where possible, data is sorted by timeline. In addition, free text-based medical reports can be parsed and searched for medical concepts and related numerical entities extracted to be used in connection with the generation of aggregate profile data. Importantly, once a comparison has been made between an aggregate profile and a specific subject profile, the aggregate profile can be amended to include the data of the specific subject profile. In this manner, the aggregate profile is "evolving" with each measurement of a subject.

In one aspect of the technology, data can be transformed in that graphical displays, plots, charts of data, etc. can be generated. Humans are known to be able to absorb a lot of visual information in a very short time frame (50% of the cerebral cortex is for vision). To assist the practitioner, presenting the information graphically rather than textually allows the healthcare provider to absorb the information quickly. Information graphics (e.g., graphical displays, plots, charts) can thus be used to show statistics or evolution of these values over time. Similarly, for grouped acts, clickable visual icons can be based on corresponding.

Figure 1:
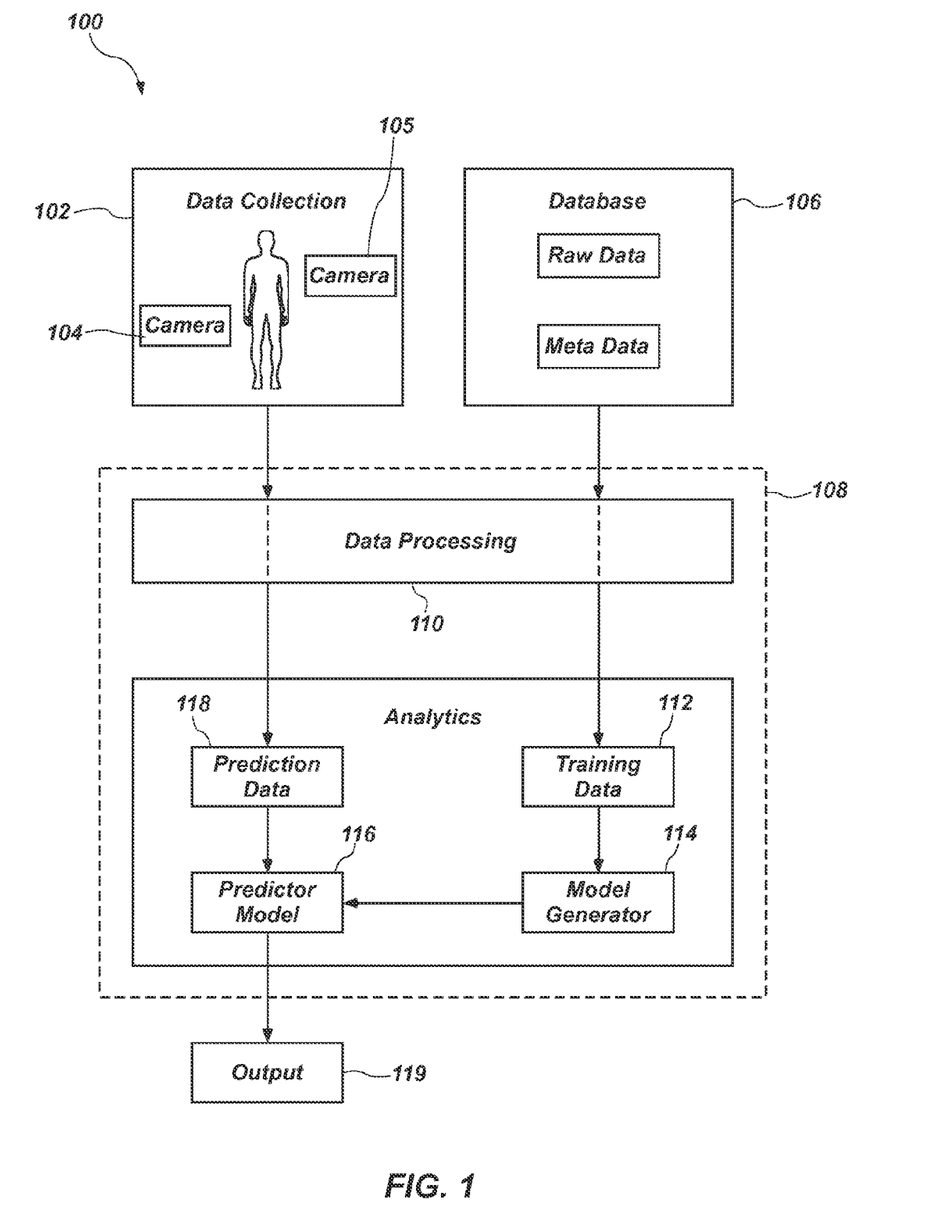
FIG. 1 is a flow chart illustrating aspects of the current technology.

With reference to FIG. 1, a generalized architecture for the present technology includes a system 100 for analyzing outward micro-variations of physiological conditions for diagnosis of the state of a subject (i.e., a mental, emotional, and/or physiological state). Starting at box 102, one or more camera devices 104, 105 are configured to capture images containing micro-variations in physiological conditions in a subject. Each of the camera devices 104, 105 generates images comprising a time series of image values.

Following the branch to the right of box 102, the output signals of camera devices 104, 105 can be sent to and stored in a memory component to create an archival database 106. Database 106 can house measurements of third-parties as well as the current subject. Database 106 can decode and store a segment of the raw data representing the signal from one or more cameras 104, 105 and meta data which can include the subjects' (or third-parties') demographic, including, but without limitation, surname, gender, ethnicity, date of birth, weight, medical history, and so on, as well as any information regarding the data collection system such as type, manufacturer, model, sensor ID, sampling frequency, and the like. One or more data segments of interest are communicated to a processor represented at 108. The processor 108 is a computing device configured to obtain data generated by the camera devices 104, 105 and to perform calculations based on the obtained data. In one embodiment, the computing device can include at least one processor 108, an interface for coupling the computing device to the database 106, and a nontransitory computer-readable medium. The computer-readable medium can have computer-executable instructions stored thereon that, in response to execution by the processor 108, cause the processor 108 to perform the described calculations on the obtained data. One example of a suitable computing device is a personal computer specifically programmed to perform the actions described herein. This example should not be taken as limiting, as any suitable computing device, such as a laptop computer, a smartphone, a tablet computer, a cloud computing platform, an embedded device, and the like, can be used in various embodiments of the present disclosure.

Another example of a processor 108 containing device is a robotic medical assistant device that is dedicated to attend to a specific subject (or set of subjects) within a predefined area of mobility of the subjects. The robotic medical assistance device can have an ambulatory or mobile device (e.g., an electric motor and wheel assembly, movable leg members) that mobilizes the robotic device about the predefined area. In another aspect, the robotic device can be mobilized about different predetermined areas at different predetermined periods of time corresponding to known movements or predictable movements of the subject. In one aspect of the technology, a camera sensor can be fixed to the robotic medical assistance device. However, in other aspects of the technology, the medical assistance device can be coupled to or in communication with (directly or indirectly as described further below) remote camera assets that are associated with the subject (i.e., the subject's own cellular phone, gaming system, laptop, personal computer, etc.). In another aspect, the medical assistance device can be coupled to or in communication with third-party remote camera assets (security cameras, cameras installed at observation facilities, hospital beds, etc.). All of the cameras captured data is processed by aspects of the present technology to provide image data for predicting/discerning the state of the subject.

In one aspect of the technology, the robotic device can be coupled via a wireless signal to a monitoring device (or collection of monitoring devices) directly coupled to a subject. For example, the robotic device can be configured to communicate with thermometers, electro-cardiograms, pulse oximeters, or other devices taking physical measurements of a subject's physiological state. In this manner, the predictive capacity of the models described herein can be further complemented with additional data from the subject. In other words, the predictive capacity of the model using micro-variations can be supplemented with physical measurements of the subject himself. In another aspect, the robotic device can comprise an input device configured to receive (and in one aspect analyze) a biological sample from the subject. For example, the robotic device can be equipped with a breathalyzer, a urine sampling device, a sweat sampling device, a lymph sampling device, a tear sampling device, a saliva sampling device, and/or a blood sampling device. This allows the robotic device to further supplement data of the subject for predictive modeling.

With reference again to FIG. 1, as described in more detail below, the time segment of archived data is preprocessed (box 110) to a form for further analyzing in accordance with the technology. The result is an altered dataset which can be referred to as "training data" (box 112) or "baseline data" retrieved from the subject himself. The training data is used to create a model that indicates the correlation between the camera data from the archive and a state of the subject. In FIG. 1, model generation is represented at 114 and the resulting model stored in the computing device is represented at 116. Returning to box 102, once the model 116 has been generated, the camera devices 104, 105 can be coupled to the processor 108 by a real-time connection, such as by a serial cable, a USB cable, a local network connection, such as a Bluetooth connection, a wired local-area network connection, a WIFI connection, an infrared connection, and the like. In another embodiment, the camera devices 104, 105 can be coupled to the processor 108 by a wide area network, such as the Internet, a WiMAX network, a 3G network, a GSM network, and the like. The camera devices 104, 105 can each include network interface components that couple each camera device 104, 105 to the processor 108. Alternatively, the camera devices 104, 105 can each be coupled to a shared networking device via a direct physical connection or a local network connection, which in turn establishes a connection to the processor 108 over a wide area network.

The direct physical connection aspects and the local area network connection embodiments can be useful in a scenario when the camera devices 104, 105 are located in close proximity to the processor 108, such as within the same examination room. The wide area network embodiments can be useful in a larger tele-health or automated diagnosis application. In this branch (the real time branch) the signals from the camera devices 104, 105 are preprocessed to the same format as the archived data during model generation, resulting in "prediction data." Ultimately the signal processing device uses the model to examine the prediction data 118 and provide an output 119 of a prediction of a state of a subject that is found to be correlated to the input from the camera(s) based on the training data (or aggregate third-party data). The states of the subject with which the present technology is concerned are those for which the correlation with the outwardly manifested micro-physiological data is established and modeled as described above. However, the linking of known states of the subject can also be taken into consideration (i.e., lack of sleep, poor diet, lack of water, history of hypoglycemia, etc.). Depending on the event and the established relationship, the output 119 can be binary (yes/no) or have more than two digital quantities to indicate a predictive probability or a degree of presence or severity. The output 119 can be on a display or by means of a signal, for example.

In one aspect of the technology, the correlation of the outwardly manifested micro-data with the occurrence of a state (e.g., heart attack, depression, etc.) of a subject can be established by a multiple regression analysis. For the analysis, let Y represent a dependent or criterion variable indicative of the medical event of interest, and let X1, X2, X3, . . . , Xn represent independent or predictor variables (i.e., the data derived from the sensor or sensors) of Y. An observation of Y coupled with observations of the independent variables Xi is a case or a run of an experiment. Typically observations of values for any given variable will form a continuous, totally-ordered set. In cases where a variable is categorical or probabilistic (such as a 0 or 1 representing presence or absence or a medical condition) a logistic function is used to represent the regression model. In experimental runs, score values of these variables are observed from a population. It is assumed that any dataset used is a sample from a population or large group. Regression is used to predict time series values of the dependent variable Y based on time series data of the independent variable X. Ideally, time series data for X will be sampled at regular intervals and will be represented by the Xi. Time series data for the dependent variable Y need not be sampled regularly. Observations of Yi and Xi will be made over a time period 0<t<T. Causality is assumed, and if Yt exists, Xt, Xt–1, 4 t–2, Xt–3, . . . X0 can be used in a multiple regression to predict it.

In accordance with one aspect of the technology, the predictor micro-variation can be sampled to obtain N samples between time t–N and time t. A spectral analysis (FFT in an exemplary embodiment) can be used to obtain the waveform frequency components which are used in the multiple regression analysis. Another variable for the multiple regression analysis is an indicator of the state of the subject at time t. This can be a binary indicator of a harmful medical condition indicating that the condition is likely present or absent, for example. The various observations can be used in the multiple regression to set the values of the various coefficients of the predictors in the linear function. The predictor values are the spectral components of the predictor signal. The result is the model that will reside in the processor. The processor derives the time lagged, spectrum analyzed predictor data signal from data processed from the camera device and uses the processor and the model to provide the output that indicates the prediction of the state (emotional, mental, physiological) of the subject. As distributed time-lagged regression is performed on the data, the time scales of the alleged correlations between the two waveforms can be much longer than their sampling frequencies, and it can be desirable to manage the number of predictors. The predictors need to cover the time-lag region in which the suspected correlation is in place.

A belief exists that use of spectral information (e.g., FFT) requires the use of many predictors in the model for the bandwidths of signals in use. However, multiple regression often benefits when less predictors can be used. The goal of reducing the independent variable set can be achieved when representative predictors are used, and when predictors can be placed in groups with similar characteristics. The placement of predictors into similar groups (i.e., subclasses of aggregate datasets) in the present technology can be achieved by the use of a clustering algorithm. Clustering algorithm group sets of observations, usually according to a parameter k representing the desired number of clusters to be found by the algorithm. Hierarchical clustering algorithms solve the clustering problem for all values of k using bottom up and top down methods. One suitable hierarchical clustering algorithm for use in the present invention is called AGNES (see L. Kaufman and P. J. Rousseeuw. Finding Groups in Data, An Introduction to Cluster Analysis, Hoboken, N.J., Wiley-Interscience, 2005, which is hereby expressly incorporated by reference herein) to cluster the spectral predictors based on three criteria obtained from a multiple regression performed on the FFT coefficients. As measures of similarity used in clustering, these criteria are the FFT index, the regression coefficient estimates themselves, and the regression coefficient t values.

In accordance with one aspect of the technology, the robotic medical assistance device can be configured to communicate with a remote computing device of a health care professional. Upon detection of a modified state of the subject that exceeds a pre-determined and established level of risk to the health or safety of the subject (or the health or safety of third-parties), the robotic medical assistance device can be configured to engage a health and safety protocol program. The health and safety protocol program, in accordance with one aspect, apportions risk and action based on a several-tiered approach. If the level of health risk to the subject is high and the treatment protocol is accompanied with a low risk to the subject if the treatment protocol is incorrect, the robotic medical assistance device can offer the treatment protocol to the subject. For example, if it is predicted that the subject is suffering from a heart attack and an aspirin is the prescribed treatment protocol, the administration of an aspirin will likely have no adverse effect to the subject if the subject is in fact not suffering from a heart attack. In contrast, if the level of health risk to the subject is high and the treatment protocol is accompanied with a high risk to the subject if the treatment protocol is incorrect, then a health professional can be contacted and clearance from the health professional is required prior to offering of the treatment protocol. For example, if the subject is believed to be suffering from a manic-depressive episode and a psychotropic drug is the prescribed treatment protocol, a medical professional would be required to provide a clearance code before the robotic assistance device could offer a prescribed treatment.

Aspects of the technology described herein have discussed the detection of microscopic temporally detected physiological variations of subjects. Profiles of temporal changes are generated and compared with a baseline to predict a state of the subject. In addition to visible physiological variations, it is to be understood that audible variations in a subject's speech can be contemplated as a physiological variation to be recorded and analyzed. In this aspect, a microphone receives and processes sound data from the subject and detects micro-variations in tone, inflection points, or other characteristics and compares it against a baseline (third-party aggregate profile or "normal" subject profile, etc.) to discern a state of the subject, or assist in discerning a state of the subject. For example, the subject's emotional, physiological or mental state (e.g., whether the subject is lying or suffering from a stroke) can be discerned by measuring micro-variations of his or her tone during speech. In one aspect, the audible variations can be the sole basis for comparative analysis and prediction of a subject state. In another aspect, the audible variations of a subject's speech can be included in a profile with other physiological parameters (i.e., pulse, skin coloring, temperature, facial movements, etc.) in further determining the mental, emotional, or physiological state of the subject. In yet another aspect, keywords can be identified from the subject's speech and used as part of the correlative analysis to discern the subject's state. For example, data from the subject can be collected that indicates the patient has slurred speech, rapid eye movement, and paralysis of the musculature on one side of the face of the subject thus suggesting the subject is suffering from a stroke. Other medical conditions are likewise detectable from the patient's physiological conditions detected using the techniques described herein.

Certain aspects of the technology reside in a method of predicting a health state (physiological, emotional, mental, etc.) of a subject. The method comprises capturing a series of images of the subject and amplifying microscopic temporal variations between the images. The amplified temporal variations can be used to generate a profile of the subject. The profile of the subject can be compared to a pre-existing aggregate profile of third-parties having a known state and/or a pre-existing baseline profile of the subject himself having a known state. A correlation between the profile of the third-parties and/or baseline profile of the subject can be made between the known health state and the amplified temporal variations. A prediction can then be made between the current microscopic temporal variations of the subject and a predicted state of the subject. Other methods of using the devices described herein will be appreciated by those of ordinary skill in the art.

The foregoing detailed description describes the technology with reference to specific exemplary aspects. However, it will be appreciated that various modifications and changes can be made without departing from the scope of the present technology as set forth in the appended claims. The detailed description and accompanying drawings are to be regarded as merely illustrative, rather than as restrictive, and all such modifications or changes, if any, are intended to fall within the scope of the present technology as described and set forth herein.

More specifically, while illustrative exemplary aspects of the technology have been described herein, the present technology is not limited to these aspects, but includes any and all aspects having modifications, omissions, combinations (e.g., of aspects across various aspects), adaptations and/or alterations as would be appreciated by those skilled in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims can be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus-function are expressly recited in the description herein. Accordingly, the scope of the technology should be determined solely by the appended claims and their legal equivalents, rather than by the descriptions and examples given above.

The invention claimed is:

1. A device configured to monitor visible physiological conditions of a subject, comprising:
   a processor;
   a camera in communication with the processor, the camera configured to capture at least a first and second image of the subject, said processor comprising executable code configured to amplify outwardly manifested microscopic temporal variations between the first and second image of the subject and generate a profile of at least one outwardly manifested microscopic temporally detected physiological variation of the subject;
   wherein said processor is further configured to compare the profile of the subject to a pre-existing first aggregate profile of a plurality of third-party subjects, said aggregate profile corresponding to the at least one outwardly manifested microscopic temporally detected physiological variation of the third-party subjects, said aggregate third-party profile corresponding to a known state of the third-party subjects;

wherein said processor is further configured to detect differences between the profile of the subject and the aggregate profile of the plurality of third-party subjects and determine a probability that a state of the subject corresponds to the known state of the third-party subjects;

an output for providing the probability that a state of the subject corresponds to the known state of the third-party subjects; and a database containing a plurality of aggregate profiles of third-party subjects corresponding to a plurality of states of the plurality of third-party subjects.

2. The device of claim 1, wherein the known state comprises one of an emotional state, a mental state, or a physiological state.

3. The device of claim 2, wherein the known state comprises a baseline state and wherein the processor is further configured to compare the profile of the subject to a pre-existing second aggregate profile of a second plurality of third-party subjects, wherein said second aggregate profile corresponds to a modified state of the second plurality of third-party subjects.

4. The device of claim 3, wherein the modified state of the second plurality of third-party subjects corresponds to a modified emotional state, a modified mental state, or a modified physiological state.

5. The device of claim 1, wherein the camera is configured to detect a first band of wavelengths of light ranging from 150 to 400 nm, a second band of wavelengths of light ranging from 400 to 700 nm and a third band of wavelengths of light ranging from 700 to 1100 nm.

6. The device of claim 3, wherein the database comprises a plurality of aggregate profiles of the first and second plurality of third-party subjects corresponding to a plurality of states of the plurality of subjects.

7. The device of claim 6, wherein at least one aggregate profile of the first or second plurality of third-party subjects in the database is modified by each generated profile of the at least one microscopic temporally detected physiological variation corresponding to the subject.

8. The device of claim 1, wherein the device further comprises a mobile assembly coupled to the camera configured to move the device about a pre-determined area corresponding to an area of movement of the subject.

9. The device of claim 8, wherein the device is configured to propel itself about a plurality of pre-determined areas during pre-determined periods of time.

10. The device of claim 1, further comprising a wireless device coupled to the processor configured to receive signals from a monitoring device coupled directly to the subject, wherein the monitoring device comprises one of a pulse oximeter, an EKG, or a thermometer.

11. The device of claim 10, further comprising an input device coupled to the camera configured to receive a biological sample from the subject, wherein the input device comprises one of a breathalyzer, a urine sampling device, a saliva sampling device, sweat sampling device, lymph sampling device, tear sampling device, or a blood sampling device.

12. The device of claim 1, wherein the processor comprises a wireless device configured to wirelessly communicate with and access image data from cameras that are not coupled to the device within a pre-determined area corresponding to an area frequented by the subject.

13. The device of claim 12, wherein the pre-existing cameras include cameras corresponding to the subject's cellular phone, personal computer device, gaming system, security system, or tablet.

14. The device of claim 1, wherein the processor comprises a wireless device configured to communicate with a remote computer device corresponding to a health care professional.

15. The device of claim 14, wherein the processor is configured to detect a modified state of the subject that creates a pre-determined level of risk to the subject and cause a pre-determined treatment to be performed on the subject based upon the level of risk to the subject created by performing the pre-determined treatment.

16. The device of claim 15, wherein when the level of risk to the subject created by performing the pre-determined treatment exceeds a threshold level of risk to the subject, the processor is configured to receive a clearance signal from a remote computer device corresponding to a health care professional prior to performing the pre-determined treatment.

17. The device of claim 1, wherein the first aggregate profile of the plurality of third-party subjects is restricted to subjects having one or more characteristics comprising at least one of age, gender, race, weight, existing disease state of subject, or medications taken by subject.

18. The device of claim 1, wherein the processor is configured to receive and store information related to activity conducted by the subject from the camera comprising the amount of sleep obtained by the subject within a pre-determined period of time and/or the subject's diet.

19. The device of claim 1, further comprising a sound recording device coupled to the processor.

20. The device of claim 19, wherein the processor is configured to amplify temporal variations between a first and second voice recording of the subject and generate a profile of at least one micro temporally detected variation of the voice of the subject.

21. The device of claim 1, wherein the output is a signal.

22. The device of claim 1, wherein the output is shown on a display.

* * * * *